(12) United States Patent
Lutti et al.

(10) Patent No.: US 10,161,853 B1
(45) Date of Patent: *Dec. 25, 2018

(54) MICROFLUIDIC PLATFORMS FOR OPTICAL BIOSENSING

(71) Applicant: University of South Florida, Tampa, FL (US)

(72) Inventors: Julie Lutti, St. Petersburg, FL (US); Jing Wang, Tampa, FL (US)

(73) Assignee: University of South Florida, Tampa, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/475,874

(22) Filed: Mar. 31, 2017

Related U.S. Application Data

(63) Continuation of application No. 14/181,149, filed on Feb. 14, 2014, now Pat. No. 9,687,847.

(60) Provisional application No. 61/764,298, filed on Feb. 13, 2013.

(51) Int. Cl.
*G01N 15/14* (2006.01)
*G01N 21/03* (2006.01)
*G01N 21/05* (2006.01)

(52) U.S. Cl.
CPC ......... *G01N 21/05* (2013.01); *G01N 15/1484* (2013.01); *G01N 21/0303* (2013.01); *G01N 2021/0346* (2013.01); *G01N 2201/0873* (2013.01)

(58) Field of Classification Search
CPC .............. G01N 21/05; G01N 15/1484; G01N 21/0303; G01N 2201/0873; G01N 2021/0346; G01N 2021/058; G01N 21/7746; G01N 21/552; B01L 3/502761; B01L 2400/086; B01L 2300/0816; B01L 2200/0668; B01L 2300/0867
See application file for complete search history.

(56) References Cited

U.S. PATENT DOCUMENTS

| | | |
|---|---|---|
| 6,583,399 B1 | 6/2003 | Hunziker |
| 6,879,752 B1 | 4/2005 | Ilchenko et al. |
| 7,259,855 B2 | 8/2007 | Fan |
| 2002/0114563 A1 | 8/2002 | Tapalian |

(Continued)

FOREIGN PATENT DOCUMENTS

WO 20100141365 A2 12/2010

OTHER PUBLICATIONS

Fan, et al., "Sensitive Optical Biosensors for Unlabeled Targets: A Review", ScienceDirect, Elsevier B. V., 2008, p. 8-26.

(Continued)

*Primary Examiner* — Lore R Jarrett
(74) *Attorney, Agent, or Firm* — Thomas | Horstemeyer, LLP (57) ABSTRACT

In one embodiment, a microfluidic platform for optical biosensing, the platform including an optical substrate, a layer provided on the substrate, and a channel formed within the layer and defined by the layer and the substrate through which fluid can flow, the channel including a channel constriction that gradually narrows along a length of the channel to a point at which the channel is physically sized and configured to trap a microsphere suspended in the fluid when the fluid flows through the channel so that the microsphere cannot pass the channel constriction.

14 Claims, 5 Drawing Sheets

(56) References Cited

U.S. PATENT DOCUMENTS

| | | |
|---|---|---|
| 2003/0174923 A1 | 9/2003 | Arnold |
| 2004/0037739 A1* | 2/2004 | McNeely .................. B01F 5/10 422/417 |
| 2005/0077513 A1 | 4/2005 | Fan |
| 2012/1019638 | 8/2012 | Nitkowski |

OTHER PUBLICATIONS

Daria, et al., "Dynamic Formation of Optically Trapped Microstructure Arrays for Biosensor Applications", ScienceDirect, Elsevier B.V., 2004.

Bange, et al., "Microfluidic Immunosensor Systems", ScienceDirect, Elsevier B. V., Biosensors Biolectronics 20, 2005, pp. 2488-2503.

Lutti, et al. "A Monolithic Optical Sensor Based on Whispering-Gallery Modes in Polystyrene Microspheres", Applied Physics Letters 93, 2008.

Lutti, "High Q Optical Resonances of Polystyrene Microspheres in Water Controlled by Optical Tweezers", Applied Physics Letters 91, 2007.

Vollmer, et al., "Protein Detection by Optical Shift of a Resonant Microcavity", Applied Phys. Letter 80, 2002.

Abdelrahman, et al., Surface Functionalization Methods to Enhance Bioconjugation in Metal-Labeled Polystyrene Particles. Macromolecules, 2011. 44: p. 4801-4813.

Armani, et al., Ultra-Hihg-Q Microcavity operation in H[sub 2] O and D[sub 2]O. Applied Physics Letters, 2005. 87: p. 151118.

Amold, et al., "MicroParticle Photophysics Illuminates Viral Bio-Sensing", The Royal Society of Chemistry, 2008., 137.

Bierie, et al., "TGF-B and Cancer", Cytokine & Growth Factor Reviews, 2006, 17 (1-2): p. 29.40.

Chao, et al., "Polymer Microring Resonators for Biochemical Sensing Applications", IEEE Journal of Selected Topics in Quantum Electronics, 2006. 12(1): p. 134-412.

Chuang, et al., A Novel Fabrication Methods of Embedded Micro-Channels by Using SU-8 Thick-Film Photoresists. Sensors and Actuators a-Physical, 2003. 103 (1-2): p. 64-69.

Fan, et al., Sensitive Optical Biosensors for Unlabeled Targets: A Review: Analytica Chimica Acta, 2008, 620: p. 8-26.

Francois, et al., "Whispering Gallery Mode Biosensor Operating in the Stimulated Emission Regime", Applied Physics Letters, 2009. 94(3): p. 031101-3.

Gregor, et al., "An Alignment-Free Fiber-Coupled Microsphere Resonator for Gas Sensing Applications", Applied Physics Letters, 2010, 96: p. 231102.

Hanahan, et al., Hallmarks of Cancer: The Next Generation. Cell, 2011. 144(5), p. 646-674.

Heideman, et al. "Remote Opto-Chemical Sensing with Extreme Sensitivity: Design, fabrication and performance of a pigtailed integrated Optical Phase-Modulated Mach-Zehnder Interferometer System", Sensors and Actuators B-Chemical, 1999. 61(1-3): p. 100-127.

Hunt, et al. "Recycling Microcavity Optical Biosensors", Opt. Letter., 2011. 36(7): p. 1092-1094.

Ioppolo, et al., "Pressure Tuning of Whispering Gallery Mode Resonators", J. Opt. Soc. A. B, 2007. 24 (10): p. 2721-2726.

Knight, J.C., et al., Mapping Whispering-Gallery Modes in Microspheres with a near-Field Probe. Optics Letters, 1995.20(14): p. 1515-1517.

Lam, C.C., P.T. Leung, and K. Young, Explicit Asymptotic Formulas for the Positions, Widths, and Strengths of Resonances in Mie Scattering. Journal of the Optical Society of America B-Optical Physics, 1992. 9(9): p. 1585-1592.

Lee M.R. and P.M. Fauchet, Nanoscale microcavity sensor for single particle detection. Optics Letters, 2007. 32(22): p. 3284-3286.

Leosson, K. and B. Agnarsson, Integrated Biophotonics with CYTOP. Micromachines, 2012. 3(1): p. 114-125.

Li, H. and X. Fan, Characterization of sensing capability of optofluidic ring resonator biosensors. Applied Physics Letters, 2010. 97(1): p. 011105.

Lu, T., et al., High sensitivity nanoparticle detection using optical microcavities. Proceedings of the National Academy of Sciences of the United States of America, 2011. 108: p. 5976-5979.

Luppa P.B., L.J. Sokoll, and D.W. Chan, Immunosensors—principles and applications to clinical chemistry. Clinica Chimica Acta, 2001. 314(1-2): p. 1-26.

Senthil Murugan, G., et al., Position-dependent coupling between a channel waveguide and a distorted microsphere resonator. Journal of Applied Physics, 2010. 107: p. 053105.

Ong, B.H., X.C. Yuan, and S.C. Tjin, Adjustable refractive index modulation for a waveguide with SU-8 photoresist by dual-UV exposure lithography. Applied Optics, 2006. 45(31): p. 8036-8039.

Shera, E.B., et al., Detection of Single Fluorescent Molecules. Chemical Physics Letters, 1990. 174(6): p. 553-557.

Shew, B.Y., et al., UV-LIGA interferometer biosensor based on the SU-8 optical waveguide. Sensors and Actuators a-Physical, 2005. 120(2): p. 383-389.

Shopova, S.I., et al., Ultrasensitive nanoparticle detection using a portable whispering gallery mode biosensor driven by a periodically poled lithium-niobate frequency doubled distributed feedback laser. The Review of scientific instruments, 2010. 81: p. 103110.

Sunkara, V., et al., Simple room temperature bonding of thermoplastics and poly(dimethylsiloxane). Lab on a Chip, 2011. 11(5): p. 962-965.

Teraoka, I., S. Arnold, and F. Vollmer, Perturbation approach to resonance shifts of whisperinggallery modes in a dielectric microsphere as a probe of a surrounding medium. Journal of the Optical Society of America B-Optical Physics, 2003. 20(9): p. 1937-1946.

Tong, L.M., et al., Self-modulated taper drawing of silica nanowires. Nanotechnology, 2005. 16(9): p. 1445-1448.

Vlachopoulou, M.E., et al., A low temperature surface modification assisted method for bonding plastic substrates. Journal of Micromechanics and Microengineering, 2009. 19(1).

Vollmer, F., S. Arnold, and D. Keng, Single virus detection from the reactive shift of a whisperinggallery mode. Proceedings of the National Academy of Sciences of the United States of America, 2008. 105(52): p. 20701-4.

Vollmer, F., et al., Protein detection by optical shift of a resonant microcavity. Applied Physics Letters, 2002. 80(21): p. 4057-4059.

Wang, S., et al., Label-free imaging, detection, and mass measurement of single viruses by surface plasmon resonance. Proceedings of the National Academy of Sciences of the United States of America, 2010. 107(37): p. 16028-32.

Ymeti, A., et al., Fast, ultrasensitive virus detection using a young interferometer sensor. Nano Letters, 2007. 7(2): p. 394-397.

Wilson, et al. Whispering Gallery Mode Biosensor Quantification of Fibronectin Adsorption Kinetics onto Alkylsilane Monolayers and Interpretration of Resultant Cellular Response, Biomaterials 33 (2012) 225-236.

Soteropulos, et al., Determination of Binding Kinetics Using Whispering Gallery Mode Microcavities. Applied Physics Letters 99, 2011.

Schneider, et al., Hartman Interferometer: Versatile Integrated Optic Sensor for Label-Free, Real-Time Quantification of Nucleic Acids, Proteins, and Pathogens. Clinical Chemistry, 1757-1763, 1997.

Nordstrom, et al., Single-Mode Waveguides with SU-8Polymer Core and Cladding for MOEMS Applications. Journal of Lightwave Technology, vol. 25, No. 5, May 2007.

Nadeau, et al., High-Q Whispering-Gallery Mode Sensor in Liquids. Jet Propulsion Laboratory, 2002.

Mott, et al., The Bulk Modulus and Poisson's Ratio of "Incompressible" Materials. Science Direct, Journal of Sound and Vibration, 2008.

* cited by examiner

MICROFLUIDIC PLATFORMS FOR OPTICAL BIOSENSING

CROSS-REFERENCE TO RELATED APPLICATION(S)

This application is a continuation application of U.S. Non-Provisional Application entitled "Microfluidic Platforms For Optical Biosensing," having Ser. No. 14/181,149 and filed Feb. 14, 2014, and claims priority to U.S. Provisional Application Ser. No. 61/764,298, filed Feb. 14, 2013, both of which are hereby incorporated by reference herein in their entireties.

BACKGROUND

Optical biosensors are powerful tools used in the analysis of biomolecular interactions, a key part of the drug discovery process. They can not only provide detailed information on the binding affinity and kinetics of the biomolecular interaction, but can also be exploited for the detection of bacteria and viruses for medical diagnosis, environmental monitoring, and homeland security.

A biosensor generally comprises a surface coated with biorecognition elements selected for their specific binding affinity with a molecule of interest (i.e., the molecule to be detected/measured). To be detected, binding must result in a physically detectable change. Optical biosensors are used to sense the local increase of refractive index that occurs near the surface as a result of the accumulation of the molecules of interest.

Optical resonator biosensors use optical resonators that exhibit sharp, i.e., high Q, optical resonances from their whispering gallery modes (WGM). Those resonances can be used for highly sensitive biodetection as they shift when small amounts of biomolecules attach to the resonator surface. As compared to planar devices, microresonator-based detectors take advantage of the recirculation of light, effectively increasing the interaction length with the sensing surface, thus yielding higher sensitivity.

Microsphere resonators made of dielectric material are particularly attractive because they can sustain high Q resonances and therefore provide more accurate results. In some cases, microspheres are placed on stems and are handled with micro-positioners. Unfortunately, it can be difficult to handle and position a microsphere in a desired manner in such circumstances because of the small size of the microsphere and the precision needed for its placement. In other cases, microspheres are permanently bonded to an optical substrate or fiber. While this can make it easier to handle and position the microsphere, such an arrangement is irreversible.

In view of the above discussion it can be appreciated that it would be desirable to have a way to easily handle and position a microsphere for optical biosensing.

BRIEF DESCRIPTION OF THE DRAWINGS

The present disclosure may be better understood with reference to the following figures. Matching reference numerals designate corresponding parts throughout the figures, which are not necessarily drawn to scale.

DETAILED DESCRIPTION

As described above, it would be desirable to have a way to more easily handle and position microspheres for optical biosensing. Disclosed herein are microfluidic platforms that can be used for this purpose. In some embodiments, a microfluidic platform comprises a microfluidic channel through which a fluid that contains one or more microspheres can flow. The channel includes a constriction that can be used to trap a single microsphere in a position that facilitates optical biosensing. In some embodiments, the constriction makes three-point contact with the microsphere and leaves a top portion of the microsphere untouched.

In the following disclosure, various specific embodiments are described. It is to be understood that those embodiments are example implementations of the disclosed inventions and that alternative embodiments are possible. All such embodiments are intended to fall within the scope of this disclosure.

The present disclosure describes microfluidic platforms designed to position stand-alone microspheres at a precise location within a microfluidic channel of the platform. The platform is designed for ease-of-use and robustness and eliminates the need for optical alignment by an end user, while employing low-cost and disposable microspheres and removing the need for surface regeneration of the optical resonator.

Figure 1:
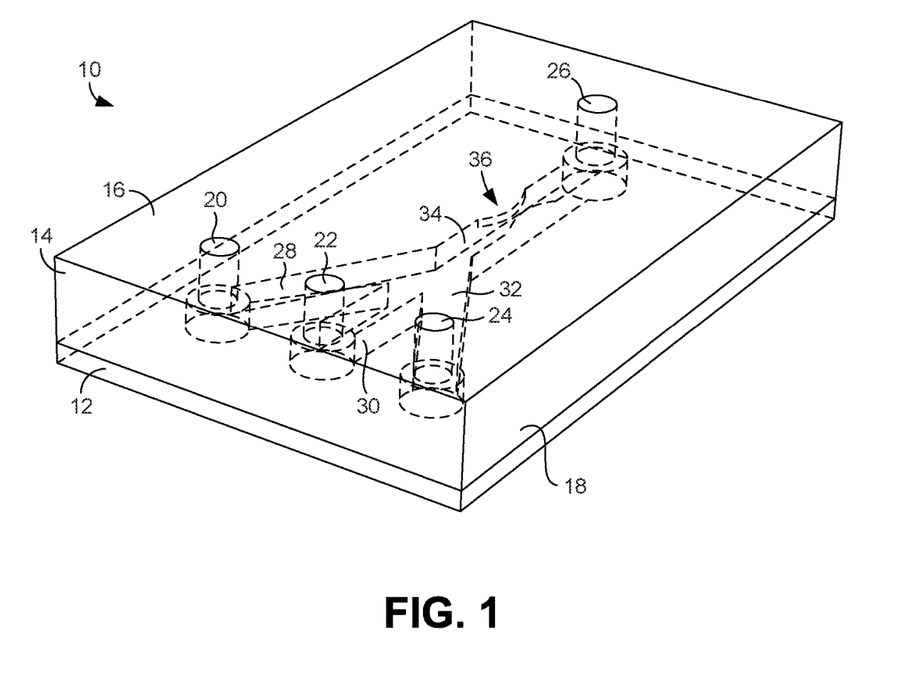
FIG. 1 is a perspective view of an embodiment of a microfluidic platform for positioning a microsphere for optical biosensing.

FIG. 1 illustrates an example embodiment of a microfluidic platform 10. As shown in this figure, the platform 10 generally comprises an optical substrate 12 on which is provided a top layer 14 that forms various channels of the platform. In some embodiments, the substrate 12 is made of a glass material having a thickness of approximately 900 to 1000 µm and an index of refraction of approximately 1.8 to 1.85. In some embodiments, the top layer 14 is made of a polymer material, such as polydimethylsiloxane (PDMS), and has a thickness of approximately 2000 to 3000 µm.

Multiple ports are formed in the top layer 14 that extend from a top surface 16 of the layer to a top surface 18 of the substrate 12. In the illustrated embodiment, these ports include a microsphere inlet 20, an analyte inlet 22, a microsphere outlet 24, and a multipurpose port 26. The purpose for each of these ports is described below. In the illustrated embodiment, each of the microsphere inlet 20, analyte inlet 22, and microsphere outlet 24 are positioned at a first end of the platform 10 and each is associated with an auxiliary channel 28, 30, and 32.

The auxiliary channels 28-32 extend from their associated ports through the top layer 14 and along the substrate 12 to a primary channel 34 that extends to the multipurpose port 26 at the other end of the platform 10. In some embodiments, the primary channel 34 is approximately 100 to 300 μm wide and 30 to 100 μm tall (e.g., 200 μm wide and 60 μm tall). As shown in FIG. 1, the primary channel 34 includes a constriction 36 in a medial position along its length that can be used to trap microspheres (one at a time) for the purpose of performing optical biosensing.

Figure 2:
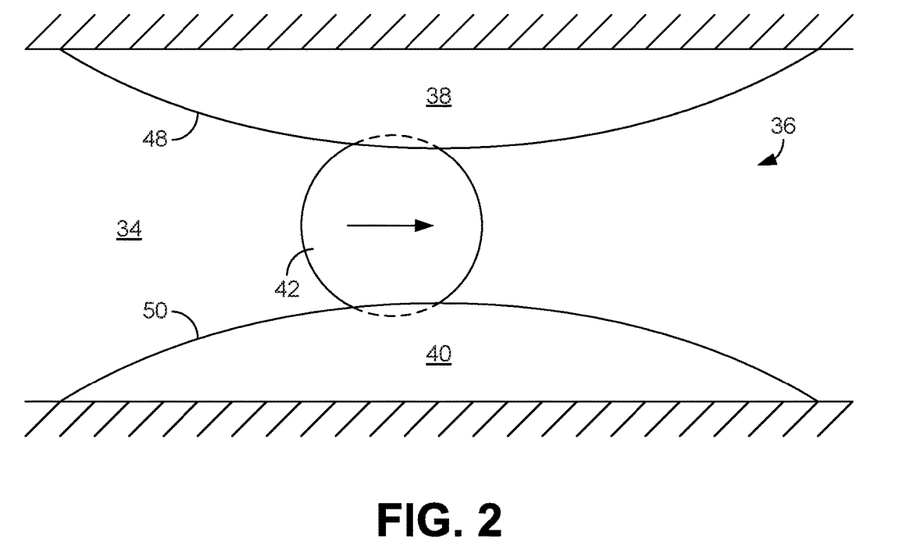
FIG. 2 is a schematic top view of a constriction of a primary channel of the microfluidic platform of FIG. 1.
Figure 3:
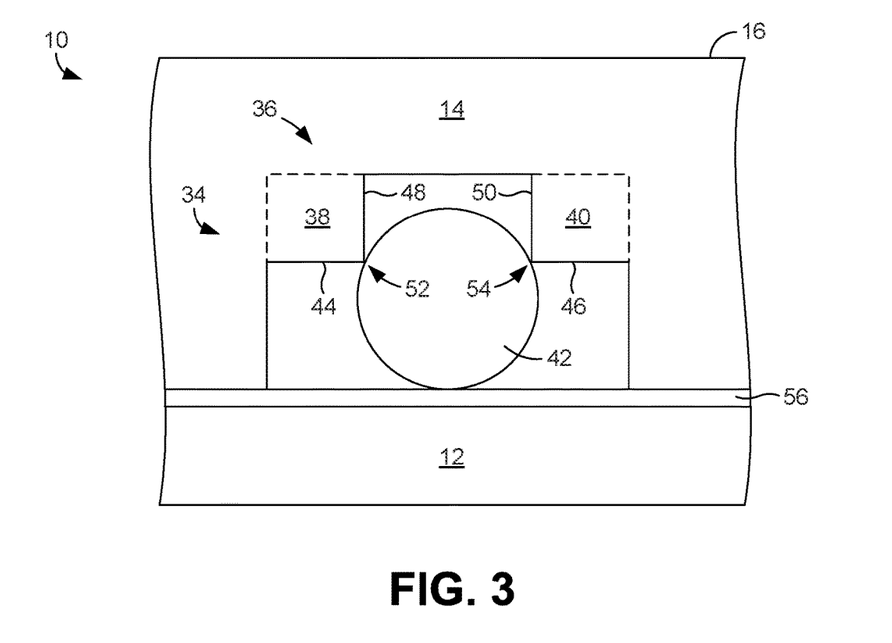
FIG. 3 is a cross-sectional view of the constriction shown in FIG. 2.

FIGS. 2 and 3 illustrate the constriction 36 from top and end views, respectively. In the embodiment of FIGS. 2 and 3, the constriction 36 has an inverted T-shaped cross section formed by two opposed inwardly-extending members 38 and 40 that gradually narrow a top portion of the primary channel 34 to a point at which a microsphere 42 can only travel along the channel to a specific position along the channel's length. In some embodiments, the inwardly-extending members 38, 40 narrow the channel 34 to approximately 25 to 300 μm. As shown most clearly in FIG. 3, the inwardly-extending members 38, 40 can be defined by horizontal lower surfaces 44 and 46 and vertical upper surfaces 48 and 50 that define 90-degree edges 52 and 54 that contact opposite sides of the microsphere 42 at a point above its center. In such a case, the microsphere 42 can be securely held in place with three contact points including the two edges 52, 54 and the substrate 12. Because the locations at which the edges 52, 54 contact the microsphere 42 only minimally overlap the excited optical mode of the microsphere, which is confined to a region near the vertical equatorial plane of the microsphere, the edges do not affect the Q-factor of the whispering gallery mode resonances.

As is further shown in FIG. 3, the surface 18 of the substrate 12 can comprise a low-index separation coating 56. In some embodiments, this coating 56 is approximately 400 nm to 600 nm thick. When the separation coating 56 is present, the microsphere 42 contacts the separation coating, which optimizes coupling of light to the microsphere. The separation coating 56 can be made of a polymeric material having an index of refraction that matches that of a liquid (e.g., water) that is used with the platform 10. In some embodiments, the separation coating 56 has an index refraction of approximately 1.33 to 1.35, which is close to the refractive index of water. By way of example, the separation coating 56 can be made of an amorphous fluoropolymer, such as Cytop®, which is available from Bellex International, Corp.

When the platform 10 is to be used for optical biosensing, a liquid (e.g., water) that contains one or more microspheres that is/are coated with suitable biorecognition elements can be delivered to the auxiliary channel 28 via the microsphere inlet 20. If the analyte inlet 22 and the microsphere outlet 24 are both closed, the liquid will flow through the primary channel 34 to the multipurpose port 26 through which the liquid can exit the platform 10. Because of the constriction 36 in the primary channel 34, however, a microsphere that travels along the primary channel 34 because of the liquid flow will become trapped by the constriction at a location at which light can be coupled with the microsphere during optical biosensing. If the liquid contains other microspheres and the clearing of those microspheres is desired, the microsphere inlet 20 can be closed, the microsphere outlet 24 can be opened, and liquid can be delivered to the primary channel 34 via the multipurpose port 26. If the flow is gentle, the trapped microsphere will remain trapped in the constriction 36, but any other microspheres in the platform 10 will be removed via the auxiliary channel 32 and the microsphere outlet 24.

Figure 4:
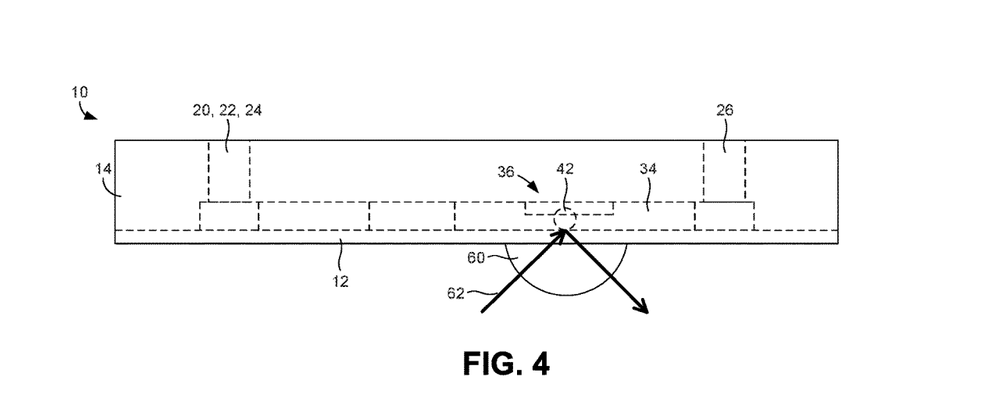
FIG. 4 is a side view of the microfluidic platform of FIG. 1 illustrating a first method for performing optical detection.
Figure 5:
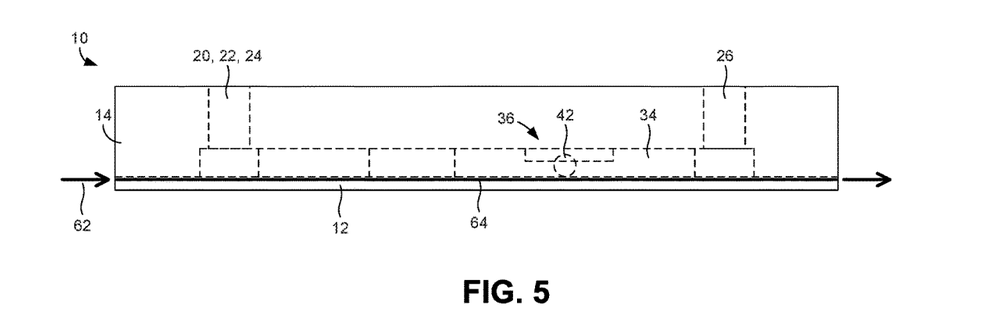
FIG. 5 is a side view of the microfluidic platform of FIG. 1 illustrating a second method for performing optical detection.

At this point, the microsphere outlet 24 can be closed and an analyte fluid that comprises molecules that will bind with the biorecognition elements on the surface of the microsphere can be delivered to the primary channel 34 via the analyte inlet 22 and the auxiliary channel 30. Optical biosensing can be simultaneously performed to determine whether or not the molecules have bound to the microsphere and, if so, to what degree. FIGS. 4 and 5 illustrate two example optical biosensing approaches.

Once the optical biosensing has been completed, the microsphere outlet 24 can be again opened and the contents of the platform 10 can be flushed by delivering fluid through the multipurpose port 26. If the flow is strong enough, the trapped microsphere will dislodge from the constriction 36 and exit the platform 10 via the microsphere outlet 24. Accordingly, the platform 10 can be described as a trap-and-release microfluidic platform.

As mentioned above, FIGS. 4 and 5 illustrate example methods for performing optical biosensing with the platform 10. Beginning with FIG. 4, optical measurements can be performed using a hemispherical prism 60 by frustrated total internal reflection. In such a case, a beam of light 62 can be directed through the hemispherical prism 60 from below the platform to enable the light to couple with the microsphere 42. In FIG. 5, the microsphere 42 is addressed using an optical waveguide 64 that is constructed on top of the substrate 12.

The microsphere used in the microfluidic platform can be made of one or more of a variety of different dielectric materials. Example materials include polystyrene and silica. The size of the microsphere, and therefore the primary channel and its constriction, can vary depending upon the particular application and microsphere material. In some embodiments, the microsphere has a diameter of approximately 25 to 500 μm.

In some embodiments, the microsphere is a polystyrene microsphere having a diameter of approximately 30 to 45 μm. Such microspheres exhibit sharp resonances and therefore hold great promise for highly sensitive biosensing. These microspheres can be surface modified for affinity-based assays. Polystyrene microspheres (cross-linked with divinylbenzene) with diameters of 45 μm have already shown a good potential for biosensing with whispering gallery mode (WGM) resonances of Q-factor in excess of $10^6$ and a demonstrated detection limit of $1.5 \times 10^{-6}$ RIU, equivalent to a surface coverage of 0.7 pg/mm$^2$. The detection limit was mostly attributed to frequency jittering of the scanning laser of about 7 MHz, while the contribution of intensity noise in the data is merely 300 kHz, corresponding to a detection limit of 0.023 pg/mm$^2$.

As indicated in Table 1, both the Q-factors and sensitivities of 45 μm spheres are on par with the most sensitive measurements reported with a 70 μm silica sphere with a detection limit of 0.028 pg/mm$^2$. However, in the latter case, substantial efforts were made to improve the stability of readily available commercial lasers by frequency doubling of a 1300 nm DFB laser. It was therefore possible to fit the position of the Lorentzian peak with a precision on the order of 460 kHz. With a laser of similar stability, the same detection limit in terms of surface coverage per unit area can be achieved with 45 μm polystyrene spheres. It should be noted that the frequency doubling technique used by Shopova et al. has the disadvantage of reducing the wavelength scanning range to just 0.1 nm, which is less than the free spectral range of the optical resonators. As a consequence, only a few of the fabricated spheres would have sharp resonances that lie in the accessible spectral range because of the inherent size variations limited by the fabrication tolerance (for all types of resonators listed).

TABLE 1

Optical resonator biosensors that have demonstrated the best detection limit.

| Technology | Reference | Loaded Q in water | sensitivity (shift in pm per pg/mm$^2$) | noise detection limit, bulk R1 sensing | noise detection limit, surface coverage | single particle detection noise limit |
|---|---|---|---|---|---|---|
| OFFR | [15] | $1.2 \times 10^5$ | 0.145 | $4 \times 10^{-8}$ | 0.14 pg/mm$^2$ | |
| microtoroid, silica | [14] | $10^8$ | | | | InfA virus 38:1 SNR- 13 ag DL |
| microsphere, silica, 300 μm | [10] | $2 \times 10^6$ | 0.011 | | 15 pg/mm$^2$ | |
| microsphere, silica, 70 μm | [17] | $10^6$ | 0.023 | $4.5 \times 10^{-8}$ | 0.28 pg/mm$^2$ | InfA virus 26:1 SNR- 20 ag DL |
| microsphere, polystyrene | [19] | $10^6$ | 0.02 | $1.5 \times 10^{-6}$ | 0.71 pg/mm$^2$ 4.5 fg | |

Because of their smaller size, 45 μm polystyrene spheres are more sensitive than 70 μm silica spheres to single particles binding at the equator, with respective shifts of 29 fm and 15 fm calculated for a single InfA virus. By further reducing the polystyrene sphere diameter from 45 μm to 25 μm, which should not affect the Q-factor, it is anticipated that the sensitivity per uniform mass coverage per unit area would be improved by two-fold, while increasing the shift associated with a single particle binding at the equator by a factor of 5 at 160 fm. Hence, a ten-fold improvement in the detection limit would be expected as compared to the work by Shopova et al. for a single particle binding at the equator, provided a laser system of similar stability is utilized.

The laser used for the optical biosensing can, in some embodiments, have a lesser stability of about 1-4 MHz when repetitively scanned over the resonance, yielding a detection limit of about 0.05 to 0.2 pg/mm$^2$ for 25 μm polystyrene microspheres. By using 25 μm polystyrene spheres, a single particle mass detection limit of 20 ag should be achievable, which is close to the best detection limit ever reported in the range of 13 ag, with the added benefit of using commercially-available tunable lasers together with low-cost and disposable stand-alone microspheres in a reusable microfluidic cell.

Microspheres made from other types of materials such as melamine and silica are also available. Some manufacturers offer microspheres made from custom monomers. Perfluorinated polymer microspheres may be of special interest because of their low material loss and may therefore hold great promise for obtaining higher Q.

A microfluidic platform having the configuration described above was fabricated for testing purposes. During the fabrication, the various channels of the platform were formed in a layer of PDMS using soft lithography. In this process, a mold was first fabricated out of SU-8 resist by photolithography on silicon. Two layers of SU-8 were used with double exposure and single development in order to define the inverted T-shape cross-section of the primary channel. PDMS was then poured onto the mold, baked, and released. The PDMS layer was then bonding to the optical substrate, which comprised a medium refractive index glass (1.41) having a spin-coated, 580 nm thick coating of Cytop® with refractive index of 1.34 to optimize optical coupling to the trapped sphere. In essence, this allows the microsphere to behave as if it is entirely surrounded by water.

The platform was tested to evaluate its trap-and-release functionality. This testing confirmed that the microsphere can be securely trapped so that, if excess microspheres accumulate, they can be flushed from the platform with gentle flow of liquid in the opposite direction without dislodging the trapped microsphere. A much stronger flow, however, was observed to release the trapped microsphere.

The WGM resonances of the microspheres were measured through the optical substrate by frustrated total internal reflection, which occurred at the interface between the high refractive index glass (1.84) and Cytop® (1.34, i.e. close to the refractive index of water). The optical set up was similar to what was reported in "High Q Optical Resonances of Polystyrene Microspheres in Water Controlled by Optical Tweezers", Applied Physics Letters, 2007, 91: p. 14116, by Lutti et al., which is hereby incorporated by reference in its entirety, with exception of the light source, which was an externally tunable diode laser (TL 6712 Velocity) emitting around 780 nm. This enabled spectral scanning without mode hopping over several free spectral ranges using motor tuning and fine scanning over a resonance using lead zirconate titanate (PZT) scanning.

The optical substrate was placed in contact with an index-matching cut ball lens that formed a hemispherical lens. The laser light was focused to a 4 μm spot at the glass-Cytop® interface with an angle of incidence of approximately 54°, i.e. in the total internal reflection regime, thus creating an evanescently decaying electromagnetic (EM) field in the Cytop® coating and water. When a microsphere was immobilized on the Cytop® surface in spatial overlap with the evanescent field, light could be coupled to the microsphere WGM at resonant frequencies, decreasing the reflected intensity. Resonance spectra were obtained by scanning the laser frequency over one or several resonances. The spot size and angle of incidence were chosen to optimize coupling to the WGMs from calculation and by experimental tuning. Both horizontal (x) and vertical (y) polarizations, which couple respectively to the transverse-magnetic (TM) and transverse-electric (TE) WGMs, were simultaneously measured by rotating the light polarization to about 45°. Because resonant frequencies are different in each polarization, one polarization can serve as a reference for light intensity when measuring resonances in the other, thus eliminating noise due to light intensity fluctuations. Hence, detection uses two photodiodes and an oscilloscope to measure the difference between the vertically and horizontally polarized reflected intensities. The WGMs in the TE and TM polarizations, respectively, appear as dips and peaks in the reflectivity spectrum obtained by scanning the laser frequency.

It is noted that the positions of the three contact points of the channel constriction preserve the integrity of the optical modes. In the case of a perfectly spherical microresonator, the resonator modes are degenerate and all modes with the same azimuthal number have the same frequency. Evanescently coupling light to the resonator at the resonant frequency by Fourier transform infrared spectroscopy (FTIR) through a prism or by coupling through a fiber excites a subset of those modes, which are in spatial overlap with the excitation. If mode matching is satisfied, then the preferentially excited mode is the equatorial mode, for which the EM field is primarily distributed around a narrow band near the equatorial plane of the sphere in the plane of incidence. When the resonator departs for perfect sphericity, the degeneracy is lifted, with the arising of several resonant frequencies that correspond to modes being various mixes of the azimuthal modes. Even in cases in which the asphericity is not known or controlled, it is more likely that the modes that can be most strongly excited via evanescent coupling with the same mode matching condition are those that have the highest content of the equatorial modes. Therefore, it is desirable that the equator does not overlap with scattering elements such as PDMS contact points, which would decrease the high Q of the resonances.

Figure 6:
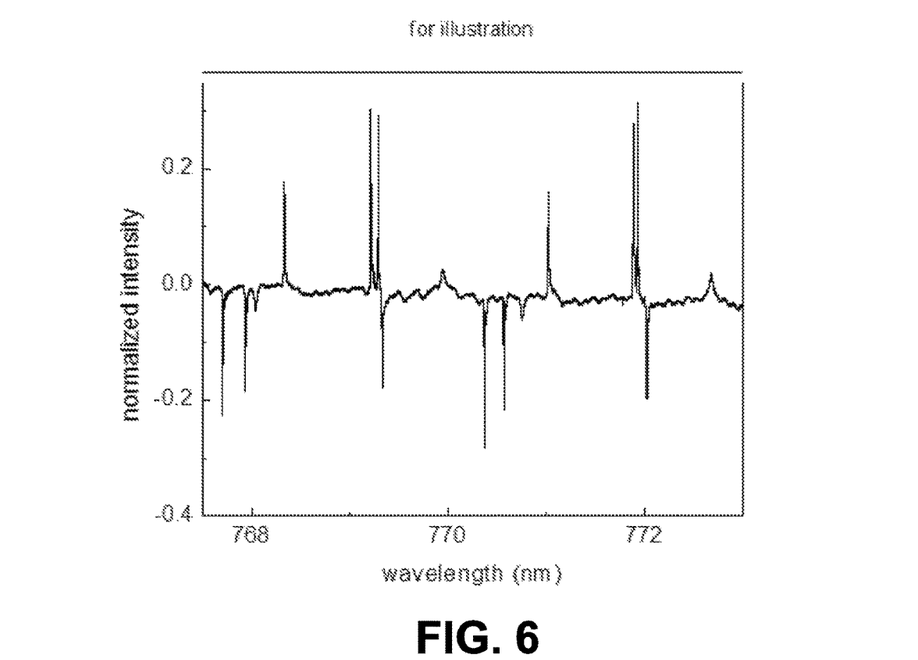
FIG. 6 is a graph that shows a typical example resonance spectrum obtained from a 45 µm polystyrene (cross-linked with divinyl benzene) microsphere trapped in a fabricated microfluidic platform.

FIG. 6 shows a typical example of a resonance spectrum obtained from a 45 µm polystyrene (cross-linked with divinyl benzene) microsphere trapped in the platform in water. The microspheres were purchased from Polysciences, Inc. The spectrum was obtained by scanning the laser wavelength using coarse motor tuning while recording the intensity reflected at the Cytop®/glass interface, as described earlier. The spectrum was calibrated using the intensity measured in the TE polarization only in the absence of a microsphere, so that an amplitude of −1 corresponds to complete extinction in the TE (resp. TM) polarization. This scan enables one to locate the resonances and determine the microsphere diameter by comparison with theory, which was determined as 45.8±0.2 µm for this microsphere.

Figure 7:
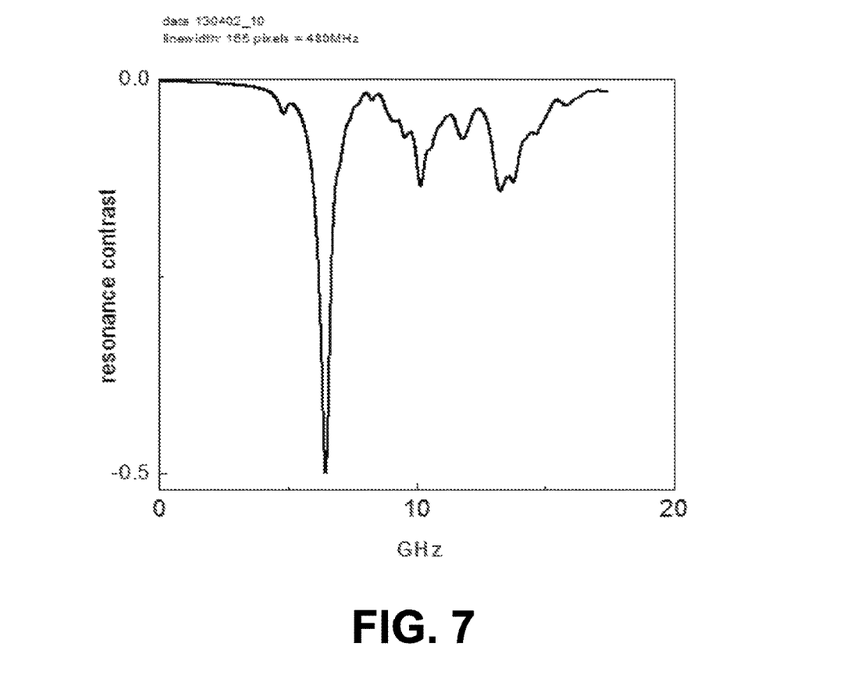
FIG. 7 is a graph that shows a resonance spectrum obtained using the fabricated microfluidic platform by performing a fine PZT wavelength scan over a selected resonance of mode number 1.
Figure 8:
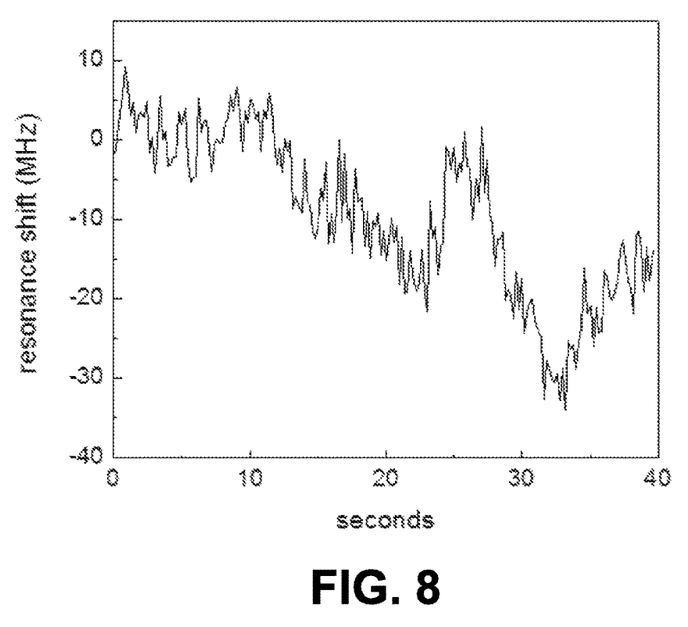
FIG. 8 is a graph that shows a measured resonance frequency with a noise RMS of 10 MHz at a repetition rate of 5 Hz.

FIG. 7 shows a resonance spectrum obtained by performing a fine PZT wavelength scan over a selected resonance of mode number 1. Using a Lorentzian line shape, the full width at half maximum (FWHM) of the main peak was 480 MHz, corresponding to a Q-factor of $0.8 \times 10^6$, which is a typical value for the microspheres that we have measured. This is consistent with typical Q-factors previously measured for the same type of microspheres while they were held at a distance from the substrate by optical tweezers, showing that the trapping method did not significantly decrease the optical mode quality. For this measurement, the center wavelength of the resonance was measured with a noise RMS of 10 MHz at a repetition rate of 5 Hz, limited by repeatability of the laser wavelength scan (FIG. 8). This translated into 1.0 pg/mm$^2$ for biosensing application.

Figure 9:
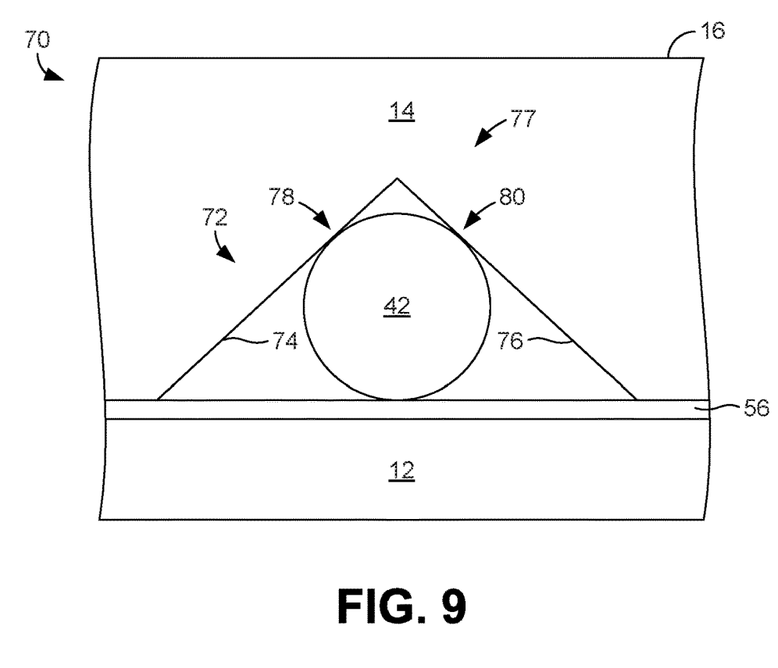
FIG. 9 is a cross-sectional view of a channel constriction of an alternative microfluidic platform.

Although a particular constriction geometry has been illustrated and described above, it is noted that alternative geometries can be used to trap and release microspheres. FIG. 9 illustrates an example of an alternative geometry. In this embodiment, a primary channel 72 of a platform 70 has a triangular cross-section formed by opposing walls 74 and 76 that form a constriction 77. The walls 74, 76 contact the microsphere 42 at opposing points 78 and 80 on opposite sides of the microsphere. Like the constriction 36 of the first embodiment, the constriction 77 does not contact the top of the microsphere 42 and therefore only minimally overlaps the excited optical mode of the microsphere.

The invention claimed is:

1. A microfluidic platform for optical biosensing, the platform comprising:
    an optical substrate;
    a layer provided on the optical substrate; and
    a channel formed within the layer and defined by the layer and the optical substrate through which fluid can flow, the channel including a channel constriction defined by a surface of the optical substrate and two opposed inwardly-extending members of the layer that extend inward from opposed lateral sides of the channel in a manner in which they gradually narrow[s] a width of the channel along its length to a point at which the channel is physically sized and configured to trap a microsphere suspended in the fluid when the fluid flows through the channel, wherein the optical substrate surface and the two opposed members together form three separate contact points of the channel constriction that are configured to contact the microsphere at three different points without any part of the channel contacting a top of the microsphere.

2. The platform of claim 1, wherein the channel at the channel constriction has an inverted T-shape in cross-section.

3. The platform of claim, 1 wherein the inwardly-extending members are defined by lower surfaces and upper surfaces that form opposing edges that contact opposite sides of the microsphere.

4. The platform of claim 3, wherein the lower surfaces are horizontal, the upper surfaces are vertical, and the edges are 90-degree edges.

5. The platform of claim 1, wherein the channel at the channel constriction has a triangular cross-section and the opposed inwardly-extending members comprise opposing walls of the layer that are angled toward each other.

6. The platform of claim 1, further comprising multiple ports formed in the layer that provide access to the channel.

7. The platform of claim 6, wherein there are multiple ports provided at a first end of the platform that provide access to a first end of the channel and a port provided at a second end of the platform that provides access to a second end of the channel.

8. The platform of claim 7, wherein the channel is a primary channel and further comprising auxiliary channels that extend from the multiple ports at the first end of the platform to the primary channel.

9. The platform of claim 1, further comprising a separation coating provided on the optical substrate and contacting the layer.

10. A microfluidic channel for trapping a microsphere, the channel comprising:
    a channel constriction that gradually narrows in width along a length of the channel to a point at which the channel is physically sized and configured to trap a microsphere having a diameter of approximately 20 to 500 microns that is suspended in a fluid when the fluid flows through the channel, wherein the channel constriction comprises a bottom surface and two opposed inwardly-extending members that extend inward from opposed lateral sides of the channel, wherein the bottom surface and the two opposed inwardly-extending members together form three contact points that are configured to contact the microsphere at three different points without any part of the channel contacting a top of the microsphere.

11. The channel of claim 10, wherein the channel at the channel constriction has an inverted T-shape.

12. The channel of claim 10, wherein the inwardly-extending members are defined by lower surfaces and upper surfaces that form edges that contact opposite sides of the microsphere.

13. The channel of claim 12, wherein the lower surfaces are horizontal, the upper surfaces are vertical, and the edges are 90-degree edges.

14. The channel of claim 10, wherein the channel at the channel constriction has a triangular cross-section and the opposed inwardly-extending members comprise opposing walls of the layer that are angled toward each other.

* * * * *